（12） United States Patent
Lai et al.

(10) Patent No.: US 7,452,491 B2
(45) Date of Patent: Nov. 18, 2008

(54) METHOD FOR FORMING SCAFFOLDS

(75) Inventors: Juin Yih Lai, Yangmei Township, Taoyuan County (TW); Ming-Hau Ho, Banciao (TW); Pei Yun Kuo, Taipei (TW); Hsyue-Jen Hsieh, Taipei (TW); Tzu-Yang Hsien, Yonghe (TW); Da Ming Wang, Yangmei Township, Taoyuan County (TW); Lein Tuan Hou, Taipei (TW)

(73) Assignee: Chung Yuan Christian University, Chung Li (TW)

( * ) Notice: Subject to any disclaimer, the term of this patent is extended or adjusted under 35 U.S.C. 154(b) by 416 days.

(21) Appl. No.: 10/844,786

(22) Filed: May 13, 2004

(65) Prior Publication Data

US 2005/0253292 A1 Nov. 17, 2005

(51) Int. Cl.
*B29C 35/16* (2006.01)
(52) U.S. Cl. .......................... 264/28; 264/86; 264/236; 264/48
(58) Field of Classification Search .................. 264/28, 264/9, 86, 637, 236, 347, 413, 48; 438/1; 427/2.14; D24/155; 525/937; 424/473
See application file for complete search history.

(56) References Cited

U.S. PATENT DOCUMENTS

| 5,628,942 | A  | * | 5/1997  | Lai et al. ..................... 264/41 |
| 5,795,920 | A  | * | 8/1998  | Kang et al. ................... 521/64 |
| 7,094,372 | B1 | * | 8/2006  | Wang et al. ................ 264/45.1 |
| 2003/0105525 | A1 | * | 6/2003  | Vyakamam et al. ...... 623/15.12 |
| 2003/0181978 | A1 | * | 9/2003  | Brown et al. ............. 623/11.11 |
| 2003/0232895 | A1 | * | 12/2003 | Omidian et al. ............... 521/99 |
| 2004/0028738 | A1 | * | 2/2004  | Huang et al. ................. 424/484 |
| 2004/0028875 | A1 | * | 2/2004  | Van Rijn et al. .............. 428/98 |
| 2005/0077232 | A1 | * | 4/2005  | Lai et al. ..................... 210/490 |
| 2005/0228173 | A1 | * | 10/2005 | Lai et al. ...................... 536/53 |

OTHER PUBLICATIONS

Ming-Hua Ho et al, Preparation of porous scaffolds by using freeze-extraction and freeze-gelation methods, Jan. 2004, vol. 25, Issue 1, 129-138.*

* cited by examiner

*Primary Examiner*—Monica A Huson
(74) *Attorney, Agent, or Firm*—WPAT., P.C.; Justin King

(57) ABSTRACT

The present invention discloses a method for forming scaffolds. This invention provides various fixation agents for different polymers or applications, and a fixation process is performed at low temperature. Moreover, the method comprises a dissolution process, a temperature adjusting process, a freezing process and a fixation process, wherein the fixation process is selected from the group of a solid-liquid exchange process, a neutralization process and a gelation process.

35 Claims, 3 Drawing Sheets

METHOD FOR FORMING SCAFFOLDS

BACKGROUND OF THE INVENTION

1. Field of the Invention

The present invention is related to a method for forming a scaffold, particularly to a scaffold-forming method that has a fixation process at low temperature.

2. Description of the Prior Art

Tissue engineering, a technique to create new tissue from cultured cells, has now been considered as a potential alternative to organ or tissue transplantation. A key technique in tissue engineering is to prepare biodegradable scaffolds with suitable structure for cell culture. The functions of scaffolds include:

a. delivering the cells or inchoate tissue to a specific location in the human body, so as to keep the cells or tissue from damages caused by the human immune system or other physical effects of the human body;

b. constructing new tissue or organs into needed three-dimensional structure and providing support and protection;

c. stimulating the cells or tissue to perform specific functions; for example, some requested effects can be achieved by coating specific signal-generating agents on scaffolds.

Conventional methods for forming scaffolds include phase separation and non-phase separation methods. The phase separation method is a method in which pores are formed via phase separation. Common examples are thermally-induced phase separation and nonsolvent-induced phase separation. On the other hand, common non-phase separation scaffold-forming methods include leaching, three-dimensional printing, gas foaming, and sintering of half-melted polymer particles.

Freeze-drying is a widely used scaffold-forming phase separation method. The method comprises two processes: the freezing process and the drying process. First of all, the temperature of the prepared polymer solution is lowered to transfer the solution from homogeneous state to heterogeneous state. While transferring, the solution is separated into two phases which are polymer-rich and polymer-poor phases. The polymer-poor phase then becomes the pores and the polymer-rich phase becomes the pore walls after the solvent is removed. In other words, the porous structure takes shape when the polymer solution is frozen. To obtain porous scaffolds, the porous structure resulted from freezing should be carefully retained during the stage of solvent removal. The reason why freeze-drying is widely used is that the solvent is vacuum-dried at a temperature low enough to prevent damage to the porous structure. Nonetheless, the freeze-drying method comes with some limitations as follows:

a. limited solvent options: to be utilized in the freeze-drying method, often a highly volatile solvent is preferred so as to avoid difficulties in solvent removal caused by the low vapor pressure at low drying temperature;

b. considerable power consumption: the freezing equipment requires huge power consumption, which is often an obstacle to large-scale production;

c. a time-consuming process: a long period of time is required to completely remove the solvent because of the inherent low volatility of solvent at low temperature; for example, a couple of days won't guarantee complete removal when a solvent with a high boiling point comes into consideration, Therefore, a new method for forming scaffolds is still needed corresponding to both economic effect and utilization in industry.

SUMMARY OF THE INVENTION

In accordance with the present invention, a new method for forming scaffolds is provided that substantially overcomes the drawbacks of the above problems mentioned from the conventional system.

One of the main objects of the present invention is, based on different polymer materials and application needs thereof, to provide different fixation agents for the fixation process at low temperature. By removing the polymer solvent (polymer-poor phase) or fixing the polymer (polymer-rich phase) in the frozen polymer solution at low temperature, the present invention is able to retain the porous structure and form a scaffold thereof. Another achievement of the present invention is a broadened range of the applicable solvents for forming scaffolds. For example, a solvent with a high boiling point may now be an option. As the number of the usable solvent increases, opportunity of finding suitable non-toxic solvents is also higher.

Accordingly, the present invention discloses a method for forming scaffolds. The provided method is simple and does not require special freeze-drying equipment. Therefore, the present invention corresponds to both economic effect and utilization in industry. The provided method comprises a dissolution process, a temperature adjusting process, a freezing process and a fixation process, wherein the fixation process is selected from the group of a solid-liquid exchange process, a neutralization process and a gelation process.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

What is probed into the invention is about a method for forming scaffolds. Detailed descriptions of the production, structure and elements will be provided in the following in order to make the invention thoroughly understood. Obviously, the application of the invention is not confined to specific details familiar to those who are skilled in the scaffolds. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Figure 1:
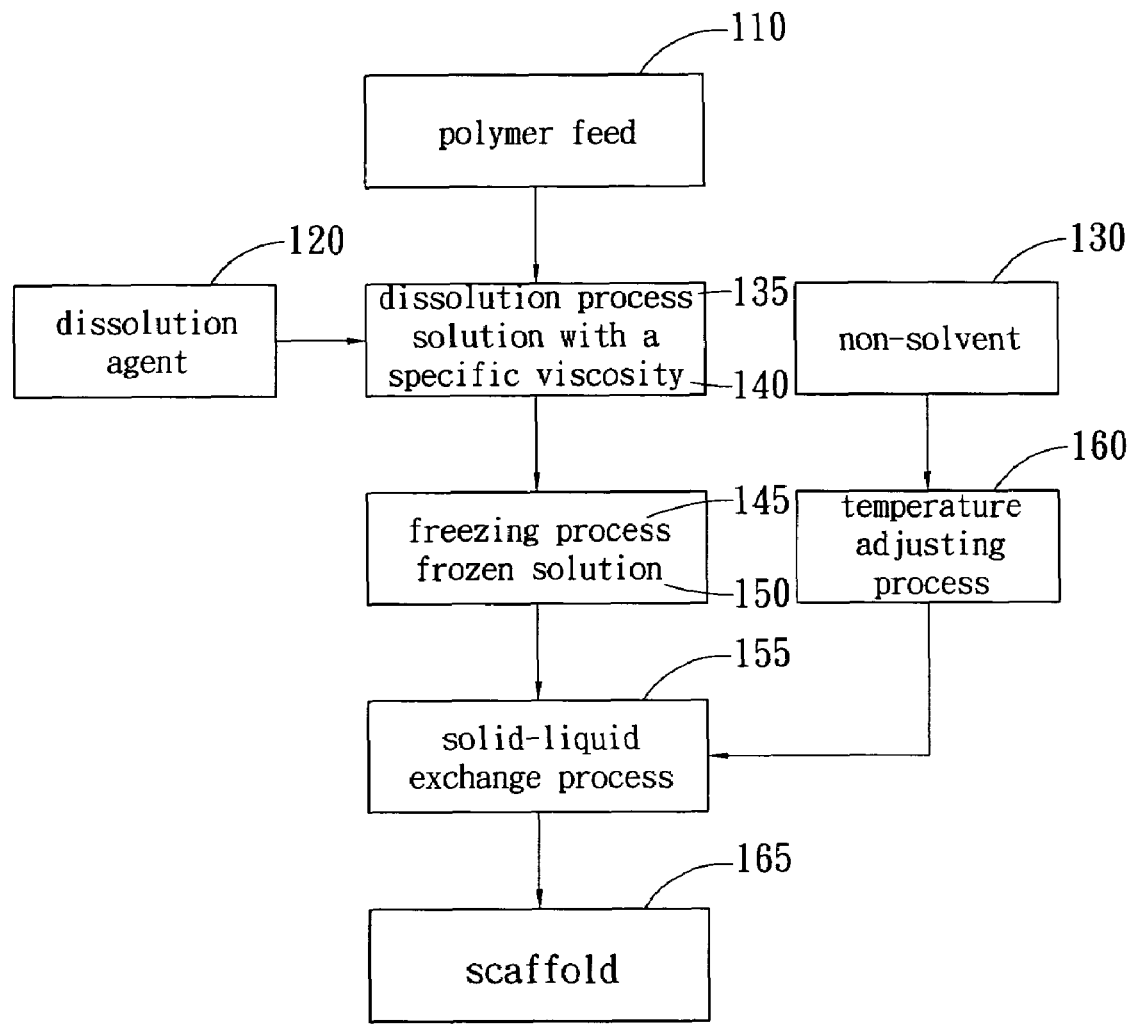
FIG. 1 shows a flowchart of a method for forming a scaffold, wherein the method comprises a solid-liquid exchange process and is provided in the first preferred embodiment of this invention.

Referring to FIG. 1, in a first embodiment of the present invention, a polymer feed 110 is provided. The polymer feed 110 comprises components selected from a group consisting of the following: polylactic acid (PLA), poly(lactide-co-glycolide) (PLGA), poly(hydroxyalkonate)s (PHA), poly(3-hydroxybutyrate) (PHB), polycaprolactone (PCL), and the derivatives thereof. PLA comprises PLLA, PDLA, and PDLLA. The frequently used solvent for PLA is 1,4-dioxane; the frequently used solvents for PLGA include Dimethylsulfoxide (DMSO), ethyl acetate, 1,4-dioxane, Dimethylformamide (DMF), and N-Methyl-Pyrrolidone (NMP); the frequently used solvents for PHA include: acetonitrile, benzene, cyclohexane, 1,4-dioxane, and Dimethylsulfoxide (DMSO); the frequently used solvents for PHB include trichloroethylene, 222-trifluoroethanol, N,N-Dimethylformamide (DMF), ethylacetoacetate, and triolein; the frequently used solvents for polycaprolactone (PCL) include: 1,4-dioxane, DMF, NMP, and DMSO.

Referring to FIG. 1, in this embodiment, the polymer feed 110 is delivered to a mixing apparatus wherein a dissolution process 135 is performed to dissolve the polymer feed 110 into a dissolution agent 120, so as to form a solution 140. The dissolution agent 120 comprises the solvent mentioned above. The solution 140 has a specific viscosity which decreases with decreasing amount of the polymer feed 110, so as to enlarge the pores of the formed scaffold. The polymer feed 110 is about 1 wt % to 15 wt % of the solution 140 when the polymer feed 110 is PLA or the derivatives thereof; the preferred range is about 3 wt % to 10 wt %. On the other hand, the polymer feed 110 is about 1 wt % to 25 wt % of the solution 140 when the polymer feed 110 is PLGA or the derivatives thereof; the preferred range is about 3 wt % to 10 wt %. Afterwards, a freezing process 145 is performed at an operation temperature for solidifying the solution 140 and forming a frozen solution 150; the frozen solution 150 has a polymer-poor phase which is to form the porous part of the formed scaffold and a polymer-rich phase which is to form the pore wall part of the formed scaffold. The pores of the scaffold are smaller if a lower operation temperature in the freezing process 145 is selected. Next, a polymer nonsolvent 130 is introduced and a temperature-adjusting process 160 is performed to adjust the temperature of the polymer nonsolvent 130 to be the same as or lower than the operation temperature in the freezing process 145. Then, a solid-liquid exchange process 155 is performed, which replaces the polymer-poor phase with the polymer nonsolvent 130 and forms the needed scaffold 165.

In this embodiment, before the freezing process 145 there may be a bubble-removing process for removing the bubbles in the solution 140. The freezing process 145 further comprises a drying procedure performed at the same operation temperature after the solution is frozen, in order to remove the polymer-poor phase matter on the surface of the frozen solution 150. Moreover, in the temperature-adjusting process 160, the polymer nonsolvent 130 is liquid at the operation temperature; or an anti-freezing agent is added to the polymer nonsolvent 130 to keep the polymer nonsolvent 130 in liquid state at the operation temperature. When the polymer feed 110 is PLA or the derivatives thereof, the selected polymer nonsolvent 130 is an alcohol aqueous solution with a concentration range from 60 wt % to 100 wt %; the preferred range is 75 wt % to 85 wt %. When the polymer feed 110 is PLGA or the derivatives thereof, the polymer nonsolvent 130 is an alcohol aqueous solution with a concentration range from 20 wt % to 50 wt %; the preferred range is 25 wt % to 35 wt %.

Figure 2:
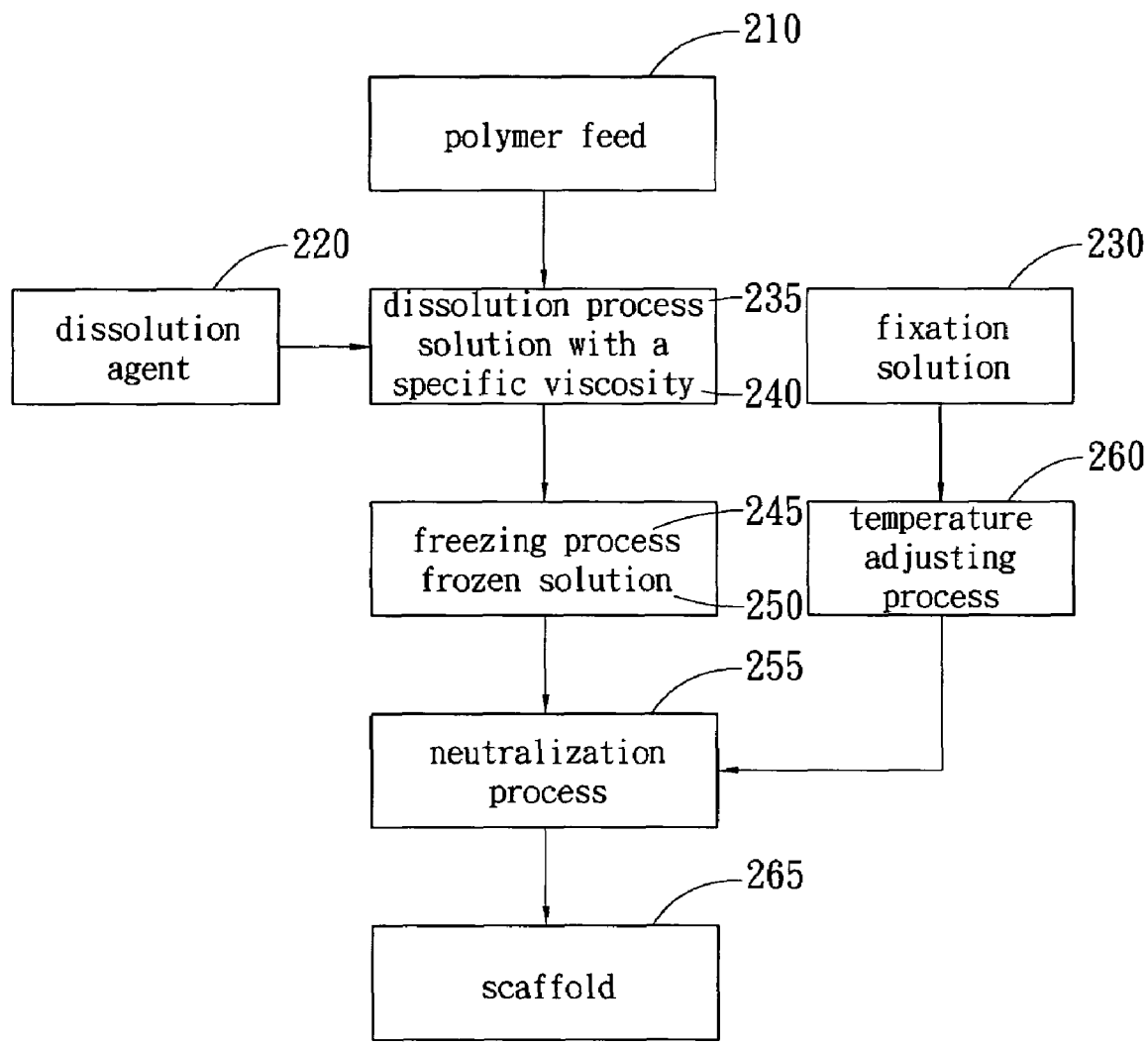
FIG. 2 shows a flowchart of a method for forming a scaffold, wherein the method comprises a neutralization process and is provided in the second preferred embodiment of this invention.

Referring to FIG. 2, in a second embodiment of the present invention, there is provided a polymer feed 210 which comprises chitosan or the derivatives thereof. The polymer feed 210 is delivered to a mixing apparatus where a dissolution process 235 is performed to dissolve the polymer feed 210 into a dissolution agent 220, so as to form a solution 240 having a specific viscosity. The dissolution agent 220 comprises the above-mentioned solvent and, the specific viscosity of the solution 240 decreases with decreasing amount of the polymer feed 210, so as to enlarge the pores of the formed scaffold. The polymer feed 210 is about 0.5 wt % to 6 wt % of the solution 240 when the polymer feed 210 is chitosan or the derivatives thereof; the preferred range is 1 wt % to 3 wt %. Afterwards, a freezing process 245 is performed at an operation temperature for solidifying the solution 240 and forming a frozen solution 250; the frozen solution 250 has a polymer-poor phase which is to form the porous part of the formed scaffold and a polymer-rich phase which is to form the pore wall part of the formed scaffold. The pores of the scaffold are smaller if a lower operation temperature in the freezing process 245 is selected. Next, a fixation solution 230 is introduced and a temperature-adjusting process 260 is performed to adjust the temperature of the fixation solution 230 to be the same as or lower than the operation temperature in the freezing process 245. What should be noticed is that if the solution 240 is acid, the fixation solution 230 is selected basic, and vice versa. For example, when the polymer feed 210 is chitosan or the derivatives thereof, the solution 240 is selected acid and the fixation solution 230 is selected basic, wherein the concentration of the basic matter in the second solution is 0.5N to 3N. Then, a neutralization process 255 is performed to solidify the polymer-rich phase matter in the frozen solution 250 with the fixation solution 230 and to form the needed scaffold 265.

In this embodiment, before the freezing process 245 there may be a bubble-removing process for removing the bubbles in the solution 240. The freezing process 245 further comprises a drying procedure performed at the same operation temperature after the solution is frozen, in order to remove the polymer-poor phase matter on the surface of the frozen solution 250. Moreover, in the temperature-adjusting process 260, the fixation solution 230 is liquid at the operation temperature; or an anti-freezing agent is added to the fixation solution 230 to keep the fixation solution 230 in liquid state at the operation temperature. The anti-freezing agent further comprises alcohol that is about 20 wt % to 70 wt % of the fixation solution 230.

Figure 3:
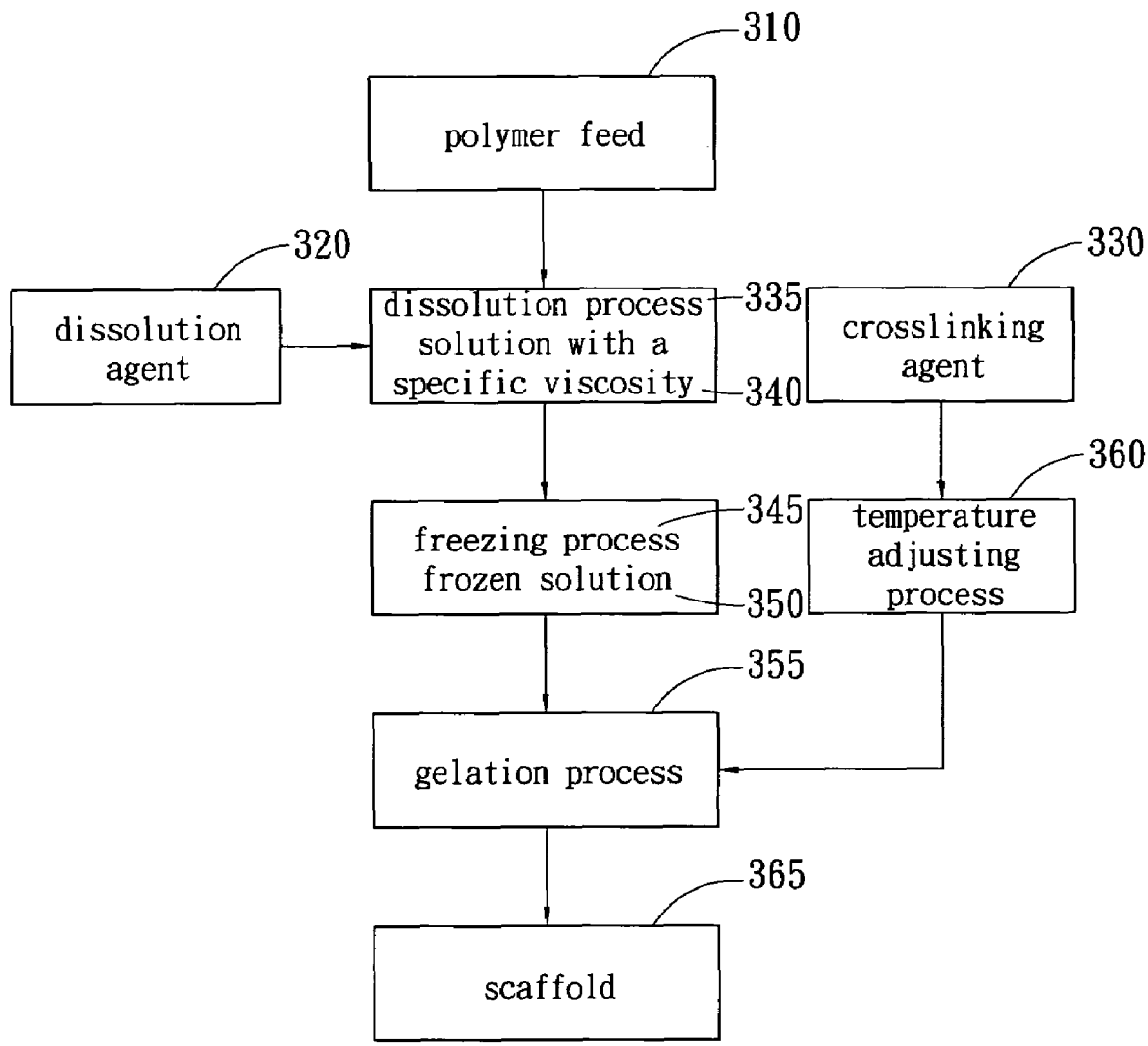
FIG. 3 shows a flowchart of a method for forming a scaffold, wherein the method comprises a gelation process and is provided in the third preferred embodiment of this invention.

Referring to FIG. 3, in a third embodiment of the present invention, a polymer feed 310 is provided. The polymer feed 310 comprises components selected from a group consisting of the following: chitosan, alginate, and the derivatives thereof. The polymer feed 310 is delivered to a mixing apparatus wherein a dissolution process 335 is performed to dissolve the polymer feed 310 into a dissolution agent 320, so as to form a solution 340. The dissolution agent 320 comprises the solvent mentioned above. The solution 340 has a specific viscosity which decreases with decreasing amount of the polymer feed 310, so as to enlarge the pores of the formed scaffold. The polymer feed 310 is about 0.5 wt % to 6 wt % of the solution 340 when the polymer feed 310 is chitosan or the derivatives thereof; the preferred range is 1 wt % to 3 wt %. On the other hand, the polymer feed 310 is about 0.5 wt % to 8 wt % of the solution 340 when the polymer feed 310 is alginate or the derivatives thereof; the preferred range is 1 wt % to 4 wt %. Afterwards, a freezing process 345 is performed at an operation temperature for solidifying the solution 340 and forming a frozen solution 350; the frozen solution 350 has a polymer-poor phase which is to form the porous part of the formed scaffold and a polymer-rich phase which is to form the pore wall part of the formed scaffold. The pores of the scaffold are smaller if a lower operation temperature in the freezing process 345 is selected. Next, a cross linking agent 330 is introduced and a temperature-adjusting process 360 is performed to adjust the temperature of the cross linking agent 330 to be the same as or lower than the operation temperature in the freezing process 345. When the polymer feed 310 is chitosan or the derivatives thereof, the cross linking agent 330 is selected from a group consisting of the following: sulfuric acid solution, aldehyde solution, dialdehyde solution and genipin solution. When the polymer feed 310 is alginate or the derivatives thereof, the cross linking agent 330 is a calcium chloride solution with a concentration being 1 wt % to 20 wt %. Then, a gelation process 355 is performed, which gels the polymer-rich phase matter with the cross linking agent 330 and forms the needed scaffold 365.

In this embodiment, before the freezing process 345 there may be a bubble-removing process for removing the bubbles in the solution 340. The freezing process 345 further comprises a drying procedure performed at the same operation temperature after the solution is frozen, in order to remove the polymer-poor phase matter on the surface of the frozen solution 350. Moreover, in the temperature-adjusting process 360, the cross linking agent 330 is liquid at the operation temperature; or an anti-freezing agent is added to the cross linking agent 330 to keep the cross linking agent 330 in liquid state at the operation temperature. The anti-freezing agent further comprises alcohol that is about 20 wt % to 70 wt % of the cross linking agent 330.

In accordance with the above-mentioned embodiments, the present invention provides, based on different polymer materials and application needs thereof, different fixation agents for the fixation process at low operation temperature. By removing the polymer-poor phase or fixing the polymer-rich phase at low operation temperatures, the present invention is able to retain the porous structure contained in the frozen solution and to form a scaffold thereof. Moreover, with the present invention, a broadened range of the applicable solvents is provided for forming scaffolds. For example, a solvent with a high boiling point may now be an option. As the number of the usable solvent increases, opportunity of finding suitable non-toxic solvents is also higher.

Accordingly, the present invention discloses a method for forming scaffolds. The provided method is simple and does not require special freeze-drying equipment. Therefore, the present invention corresponds to both economic effect and utilization in industry. The provided method comprises a dissolution process, a temperature-adjusting process, a freezing process and a fixation process, wherein the fixation process is selected from the group of a solid-liquid exchange process, a neutralization process and a gelation process.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for forming scaffolds, comprising:
   providing a polymer feed and a dissolution agent;
   utilizing said dissolution agent to dissolve said polymer feed and form a solution with a specific viscosity;
   performing a freezing process at an operation temperature to solidify said solution and form a frozen solution with a polymer-rich phase and a polymer-poor phase wherein said polymer-poor phase is to form the porous part of the scaffold and said polymer-rich phase is to form the pore wall part of the scaffold;
   providing a polymer nonsolvent and adjusting the temperature of said polymer nonsolvent to be the same as or lower than said operation temperature in said freezing process; and
   performing a solid-liquid exchange process to replace said dissolution agent with said polymer nonsolvent and to form scaffolds.

2. The method according to claim 1, wherein said viscosity of said solution decreases with decreasing amount of said polymer feed, so as to enlarge the pores of the formed scaffold.

3. The method according to claim 1, further comprising the step of removing bubbles formed in said solution, wherein said step of removing said bubbles is performed before said freezing process.

4. The method according to claim 1, wherein the pores of the formed scaffold are smaller when lower said operation temperature is selected.

5. The method according to claim 1, wherein said freezing process further comprises a drying procedure which is performed at said operation temperature for vaporizing said polymer-poor phase matter on the surface of said frozen solution.

6. The method according to claim 1, wherein said polymer nonsolvent is liquid at said operation temperature.

7. The method according to claim 1, wherein said polymer nonsolvent further comprises an anti-freezing agent to keep said polymer nonsolvent in liquid state at said operation temperature.

8. The method according to claim 1, wherein said polymer feed is selected from a group consisting of the following: PLA, PLGA, PHA, PHB, PCL, and the derivatives thereof.

9. The method according to claim 8, wherein said polymer nonsolvent is an alcohol aqueous solution with a concentration range from about 60 wt % to 100 wt % when said polymer feed is PLA or the derivatives thereof.

10. The method according to claim 8, wherein said polymer nonsolvent is an alcohol aqueous solution with a preferred concentration range from about 75 wt % to 85 wt % when said polymer feed is PLA or the derivatives thereof.

11. The method according to claim 8, wherein said polymer nonsolvent is an alcohol aqueous solution with a concentration range from about 20 wt % to 50 wt % when said polymer feed is PLGA or the derivatives thereof.

12. The method according to claim 8, wherein said polymer nonsolvent is an alcohol aqueous solution with a preferred concentration range from about 25 wt % to 35 wt % when said polymer feed is PLGA or the derivatives thereof.

13. A method for forming scaffolds, comprising:
   providing a polymer feed and a dissolution agent;
   utilizing said dissolution agent to dissolve said polymer feed and form a first solution with a specific viscosity;
   performing a freezing process at an operation temperature to solidify said first solution and form a frozen solution with a polymer-rich phase and a polymer-poor phase wherein said polymer-poor phase is to form the porous part of the scaffold and said polymer-rich phase is to form the pore wall part of the scaffold;
   providing a fixation solution and adjusting the temperature of said fixation solution to be the same as or lower than said operation temperature in said freezing process; and
   performing an acid-base neutralization process to solidify said polymer-rich phase matter and to form scaffolds.

14. The method according to claim 13, wherein said viscosity of said first solution decreases with decreasing amount of said polymer feed, so as to enlarge the pores of the formed scaffold.

15. The method according to claim 13, further comprising the step of removing bubbles formed in said first solution, wherein said step of removing bubbles is performed before said freezing process.

16. The method according to claim 13, wherein the pores of the formed scaffold are smaller when lower said operation temperature is selected.

17. The method according to claim 13, wherein said freezing process further comprises a pre-drying procedure which is performed at said operation temperature for vaporizing said polymer-poor phase matter on the surface of said frozen solution.

18. The method according to claim 13, wherein said fixation solution is liquid at said operation temperature.

19. The method according to claim 13, wherein said fixation solution further comprises an anti-freezing agent to keep said fixation solution in liquid state at said operation temperature.

20. The method according to claim 19, wherein said anti-freezing agent comprises alcohol that is about 20 wt % to 70 wt % of said fixation solution.

21. The method according to claim 13, wherein said first solution is acid and said fixation solution is basic.

22. The method according to claim 13, wherein said first solution is basic and said fixation solution is acid.

23. The method according to claim 21, wherein said polymer feed is chitosan or the derivatives thereof.

24. The method according to claim 23, wherein the concentration of the basic matter in said fixation solution is about 0.5N to 3N.

25. A method for forming scaffolds, comprising:
   providing a polymer feed and a dissolution agent;
   utilizing said dissolution agent to dissolve said polymer feed and form a solution with a specific viscosity;
   performing a freezing process at an operation temperature to solidify said solution and form a frozen solution with a polymer-rich phase and a polymer-poor phase wherein said polymer-poor phase is to form the porous part of the scaffold and said polymer-rich phase is to form the pore wall part of the scaffold;
   providing a crosslinking agent and adjusting the temperature of said crosslinking agent to be the same as or lower than said operation temperature in said freezing process; and
   performing a gelation process to utilize said crosslinking agent for gelling said polymer-rich phase matter and forming scaffolds.

26. The method according to claim 25, wherein said viscosity of said solution decreases with decreasing amount of said polymer feed, so as to enlarge the pores of the formed scaffold.

27. The method according to claim 25, further comprising the step of removing bubbles formed in said solution, wherein said step of removing said bubbles is performed before said freezing process.

28. The method according to claim 25, wherein the pores of the formed scaffold are smaller when lower said operation temperature is selected.

29. The method according to claim 25, wherein said freezing process further comprises a pre-drying procedure which is performed at said operation temperature for vaporizing said polymer-poor phase matter on the surface of said frozen solution.

30. The method according to claim 25, wherein said crosslinking agent is liquid at said operation temperature.

31. The method according to claim 25, wherein said crosslinking agent further comprises an anti-freezing agent to keep said crosslinking agent in liquid state at said operation temperature.

32. The method according to claim 31, wherein said anti-freezing agent comprises alcohol that is about 20 wt % to 70 wt % of said crosslinking agent.

33. The method according to claim 25, wherein said polymer feed is chitosan or the derivatives thereof.

34. The method according to claim 25, wherein said polymer feed is alginate or the derivatives thereof.

35. The method according to claim 34, wherein said crosslinking agent is a calcium chloride solution and the concentration range of calcium chloride is from about 1 wt % to 20 wt %.

* * * * *